United States Patent [19]

Huang et al.

[11] Patent Number: 5,093,350

[45] Date of Patent: Mar. 3, 1992

[54] DEHYDROCYCLOCLAUSENAMIDE, ITS PREPARATION AND USE IN TREATING CEREBRAL HYPOXIA

[75] Inventors: Liang Huang; Geng-tao Liu, both of Beijing, China

[73] Assignees: Bayer Aktiengesellschaft, Leverkusen, Fed. Rep. of Germany; Chinese Academy of Medical Sciences, Beijing, China

[21] Appl. No.: 559,749

[22] Filed: Jul. 30, 1990

[30] Foreign Application Priority Data

Aug. 19, 1989 [DE] Fed. Rep. of Germany ....... 3927367

[51] Int. Cl.$^5$ .................. C07D 497/08; A61K 31/40
[52] U.S. Cl. .................................. 514/411; 548/453; 548/530; 548/544
[58] Field of Search .................. 548/453; 514/411

[56] References Cited

FOREIGN PATENT DOCUMENTS 0053699  5/1981  Japan ................................. 548/453
3072689  4/1988  Japan ................................. 548/453

Primary Examiner—David B. Springer
Attorney, Agent, or Firm—Sprung, Horn, Kramer & Woods

[57] ABSTRACT

Processes for the preparation of compounds of the formula

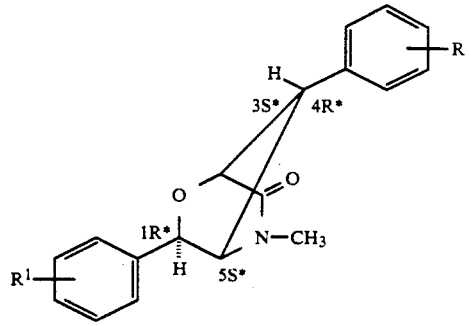

in which R and $R^1$ are identical or different and represent hydrogen or halogen, in the racemic form or in the form of its pure enantiomers by cyclicizing compounds of the formula

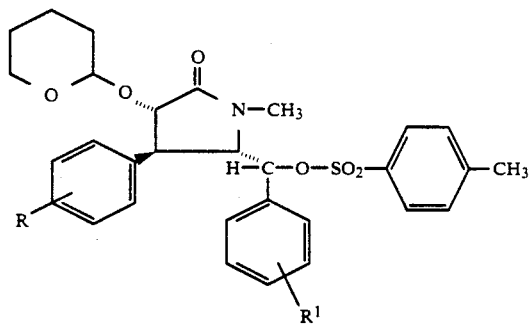

with 2,6-lutidine or by cyclicizing compounds of the formula

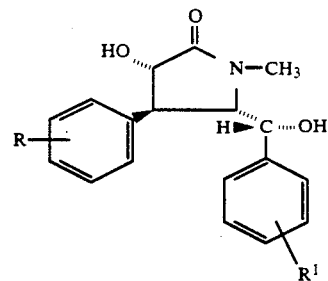

with diethyl azodicarboxylate. Compounds where R is halogen are new and are useful as cerebral therapeutics, nootropics or in the reduction of increased glutamine pyruvate transaminase in serum.

11 Claims, No Drawings

DEHYDROCYCLOCLAUSENAMIDE, ITS PREPARATION AND USE IN TREATING CEREBRAL HYPOXIA

The invention relates to a process for the preparation of dehydrocycloclausenamide and its derivatives in the racemic form and as optically active (+)-or (−)-enantiomers.

It is already known that dehydrocycloclausenamide has been obtained from the aqueous extract of leaves of Clausena lansium (low) skeels and its structure has been elucidated by means of chemical reactions and by means of X-ray structural analysis [cf. De-A1 3,431,257, Phytochemistry, 27 (2), 445–450]. It is furthermore known that dehydrocycloclausenamide suppresses the high serum level of glutamine pyruvate transaminase induced by carbon tetrachloride.

As relatively large amounts are required for pharmacological studies, but on the other hand as only 1.5 g of dehydrocycloclausenamide are obtained from 14 g of dried leaves owing to the complicated extraction process, it was necessary to make available a process for chemical synthesis and derivatization.

It is to be expressed as surprising that, with the aid of the process according to the invention, the compound of the general formula (I) according to the invention

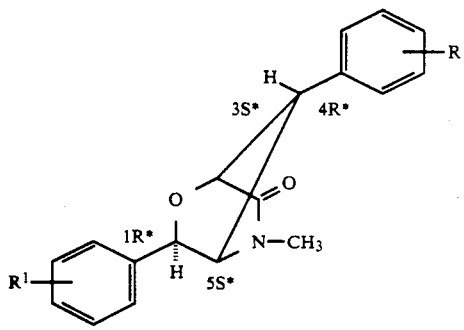

(I)

in which R and $R^1$ are identical or different and represent hydrogen or halogen, can be obtained both in the racemic form and in the form of its pure enantiomers.

The product (Ia)

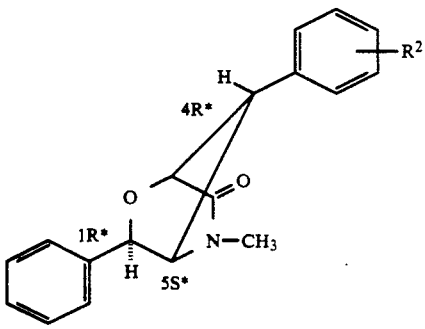

(Ia)

in which $R^2$ represents hydrogen is identical to the dehydrocycloclausenamide obtained from the plant extract. In comparison to the extraction process, larger amounts can be made available in a shorter time and with less expenditure using the new process and access to new derivatives can be facilitated.

The invention relates primarily to new compounds of the general formula (Ib)

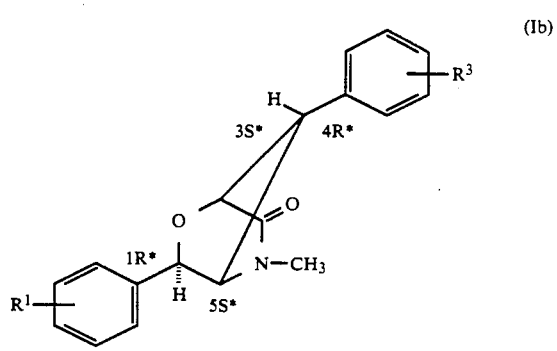

(Ib)

in which $R^3$ represents halogen and $R^1$ has the abovementioned meaning as the racemate and as the (+)- or (−)-enantiomer.

Halogen preferably represents fluorine or chlorine.

The invention furthermore relates to a process for the preparation of dehydrocycloclausenamide and its chemically synthesizable derivatives of the general formula (I).

The compounds of the general formula (I), as the (+)- and (−)-enantiomers or as the racemate (±), can be prepared by a process in which

[A] compounds of the general formula (II)

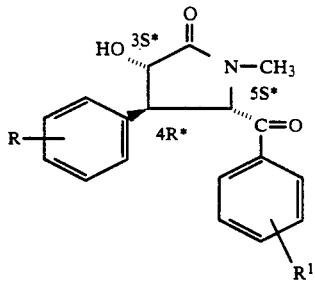

(±), (+), (−) (II)

(R,S nomenclature is shown by way of example in the compounds of the general formula (II))

in which

R represents hydrogen or halogen and $R^1$ has the abovementioned meaning either as the racemate (±) or as the corresponding (+)-or (−)-enantiomer, are etherified first with 2,3-dihydropyran to give compounds of the general formula (III)

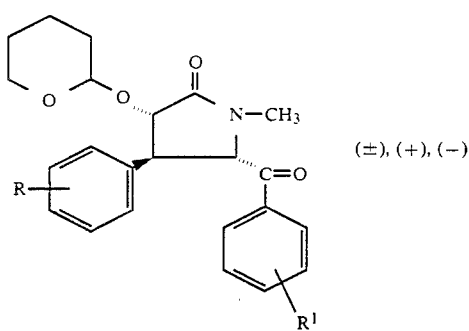

(III)

(±), (+), (−)

in which R and R¹ have the abovementioned meaning, which are then reduced by customary methods to give compounds of the general formula (IV)

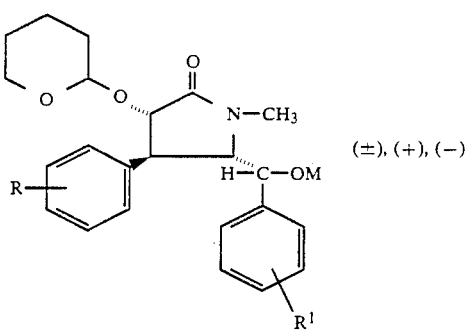

(IV)

(±), (+), (−)

in which
M represents a metal, preferably an alkali metal, zinc or aluminum,
R and R¹ have the abovementioned meaning, which are then reacted in a further step with p-methyltoluenesulphonyl chloride of the formula (V)

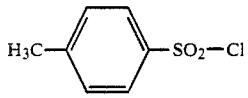

(V)

to give compounds of the general formula (VI)

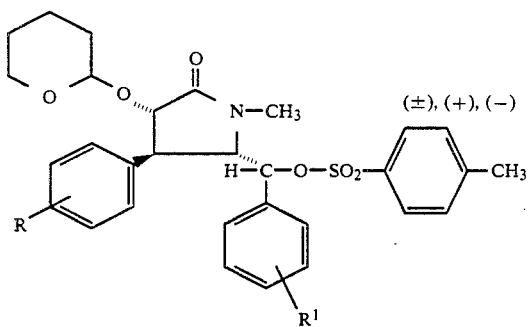

(VI)

(±), (+), (−)

in which R and R¹ have the abovementioned meaning, then the tetrahydropyranyl protective group is removed according to customary methods and in a last step the compound formed is reacted with 2,6-lutidine of the formula (VII)

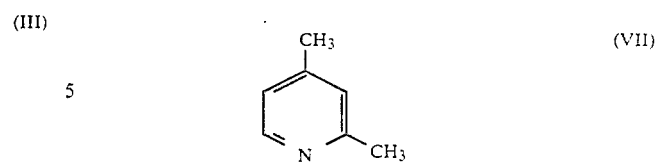

(VII)

or by a process in which
[B] compounds of the general formula (IVa)

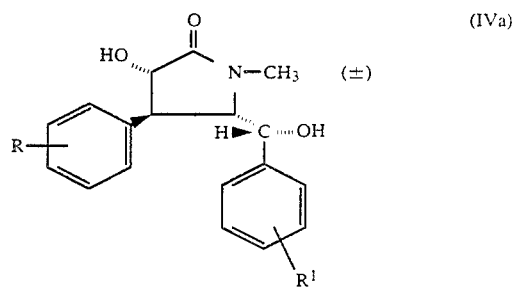

(IVa)

(±)

in which R and R¹ have the abovementioned meaning, in the racemic form (±) are reacted with diethyl azodicarboxylate of the formula (VIII)

(VIII)

if appropriate in the presence of an auxiliary, in inert solvents.

The process according to the invention can be illustrated by the following equation:

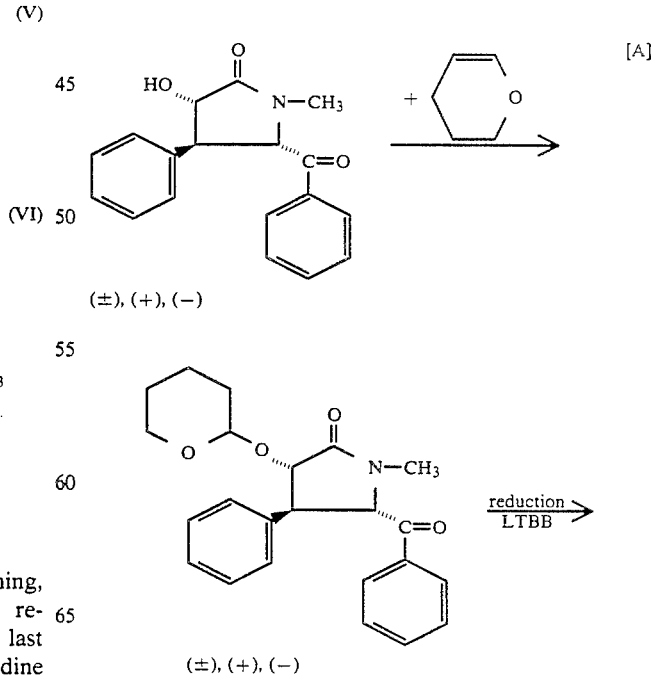

-continued

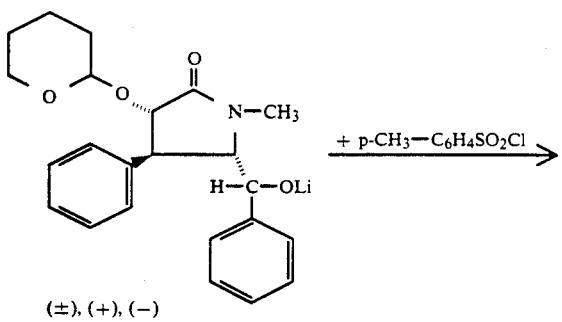
(±), (+), (−)

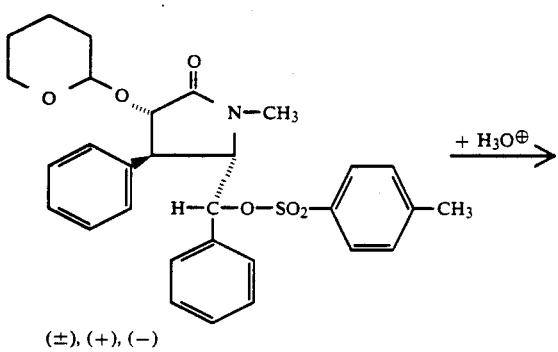
(±), (+), (−)

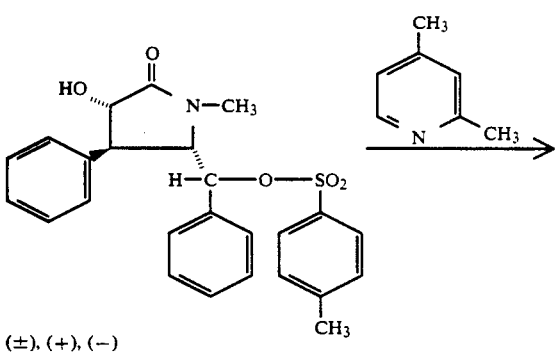
(±), (+), (−)

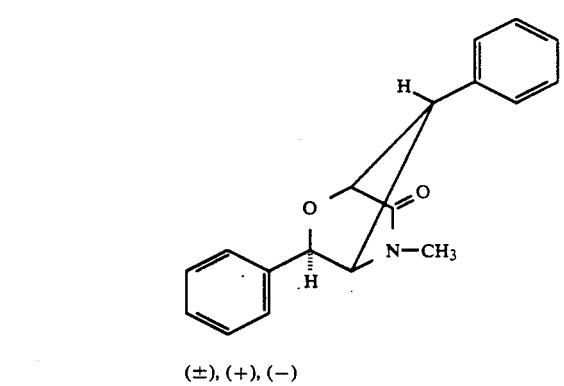
(±), (+), (−)

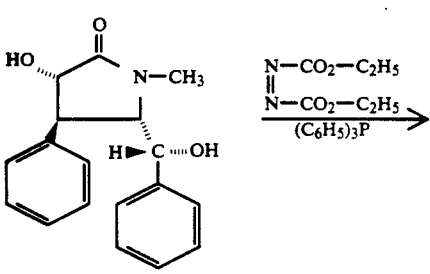

-continued

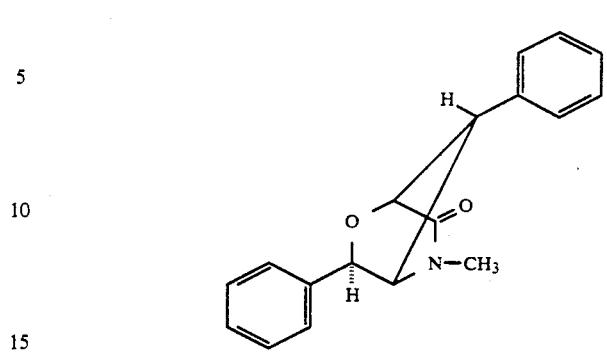

Suitable solvents for the etherification with 2,3-dihydropyran are all inert organic solvents which do not change under the reaction conditions. These preferably include halogenated hydrocarbons, such as, for example, methylene chloride or chloroform, or amides such as hexamethylphosphoramide or dimethylformamide. Methylene chloride is particularly preferred.

The etherification proceeds in a temperature range from −10° C. to +50° C., preferably at +30° C., at normal pressure.

Suitable auxiliaries are optionally sulphonic acids such as, for example, methanesulphonic acid, ethanesulphonic acid, benzenesulphonic acid or toluenesulphonic acid, or the corresponding pyridinium salts such as, for example, pyridinium p-toluenesulphonate. Pyridinium p-toluenesulphonate is preferred.

Suitable solvents for the reduction are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoramide, or dimethylformamide or acetic acid. It is also possible to use mixtures of the solvents mentioned. Diethyl ether and tetrahydrofuran are preferred.

The reduction of the keto function to the hydroxyl function can be carried out using the customary reducing agents. Particularly suitable reducing agents are metal hydrides and complex metal hydrides such as, for example, lithium borohydrides, sodium borohydrides, lithium aluminum hydride, zinc borohydrides or aluminum triisopropoxide. Lithium borohydride, sodium borohydride, zinc borohydride and aluminum triisopropoxide are particularly preferred.

The reduction can be carried out at normal pressure, but also at elevated or reduced pressure (for example 0.5–5 bar). In general, it is carried out at normal pressure.

The reaction with p-tosyl chloride proceeds in one of the abovementioned solvents at a reaction temperature of −30° C. to 0° C. at normal pressure, preferably in
[B] tetrahydrofuran at a temperature of −20° C. to −5° C. at normal pressure.

The removal of the protective group tetrahydropyranyl is carried out in a manner known per se, for example with protonic acids. These preferably include inorganic acids such as, for example, hydrochloric acid or sulphuric acid.

The reaction with 2,6-lutidine (2,6-dimethylpyridine) also takes place in one of the abovementioned inert solvents, preferably in methylene chloride, under a protective gas atmosphere. The reaction temperature is +90° C. to +170° C., preferably +100° C. to +150° C. The reaction is basically carried out at normal pressure.

The reaction with azodicarboxylic acid ester proceeds in one of the abovementioned inert solvents, preferably in tetrahydrofuran, in a temperature range from −10° C. to +60° C., preferably from 0° C. to +30° C. The reaction can be carried out both at normal pressure and at elevated or reduced pressure. It is preferably carried out at normal pressure.

Auxiliaries employed in this case are trialkylphosphanes such as, for example, triphenylphosphane or ethyldiphenylphosphane, preferably triphenylphosphane.

The compounds of the general formula (II) are known as substances per se [compare DE-A1 3,431,257], but can now be prepared chemically by cyclizing compounds of the general formula (IX)

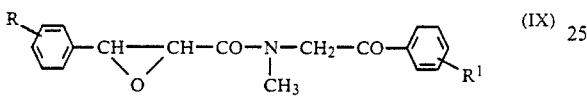

in which R and R¹ have the abovementioned meaning, in inert solvents, if appropriate in the presence of a base, and chromatographically separating the resulting isomers by customary methods.

Suitable solvents for the cyclization are inert organic solvents such as ethers, for example tetrahydrofuran, diethyl ether or dioxane, or alcohols such as, for example, methanol or ethanol, or halogenated hydrocarbons such as, for example, methylene chloride or carbon tetrachloride, or their mixtures, if appropriate also with water. Tetrahydrofuran, methanol and methylene chloride are preferred.

Suitable bases for the cyclization are alkali metal alkoxides, alkali metal amides or alkali metal hydrides such as, for example, sodium ethoxide, sodium methoxide, potassium butoxide, sodium butoxide or lithium butoxide, lithium hydroxide, sodium hydroxide or potassium hydroxide, sodium hydride, lithium diisopropylamide, butyllithium or ammonium hydroxides such as, for example, tetramethylammonium hydroxide. Lithium diisopropylamide, sodium methoxide, lithium hydroxide or tetramethylammonium hydroxide are preferred.

The reaction temperatures are between −70° C. and +40° C. The reaction is preferably carried out between −65° C. and +30° C.

The cyclization can be carried out at normal pressure, but also at elevated or reduced pressure. In general, it is carried out at normal pressure.

The pure (+)- or (−)-enantiomers of the compounds of the general formula (II) can be prepared by starting from the racemate of the compounds of the general formula (II)

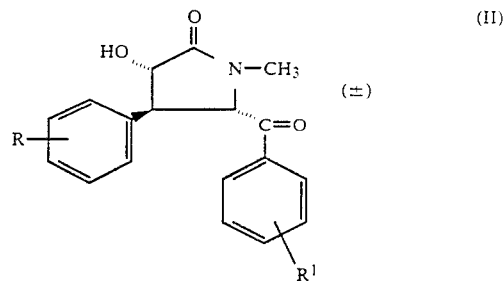

in which R and R¹ have the abovementioned meaning, preparing the corresponding diastereomers by reaction with (−)-menthoxyacetyl chloride of the general formula (X)

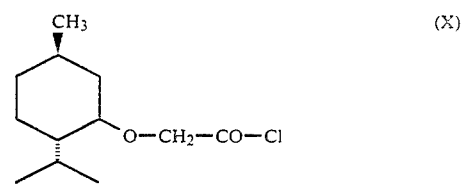

in one of the abovementioned inert solvents, preferably methylene chloride in the presence of a base, and then removing the menthoxyacetyl radical with acids with the liberation of the hydroxyl function.

The process can be illustrated by the following equation:

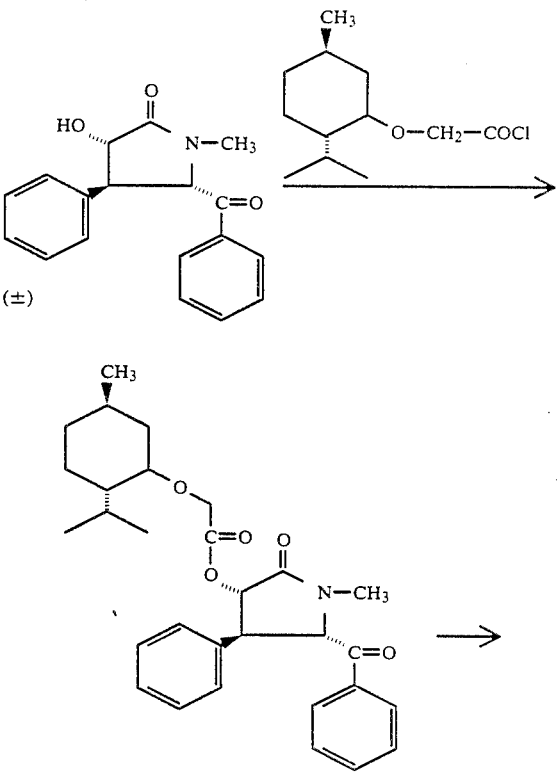

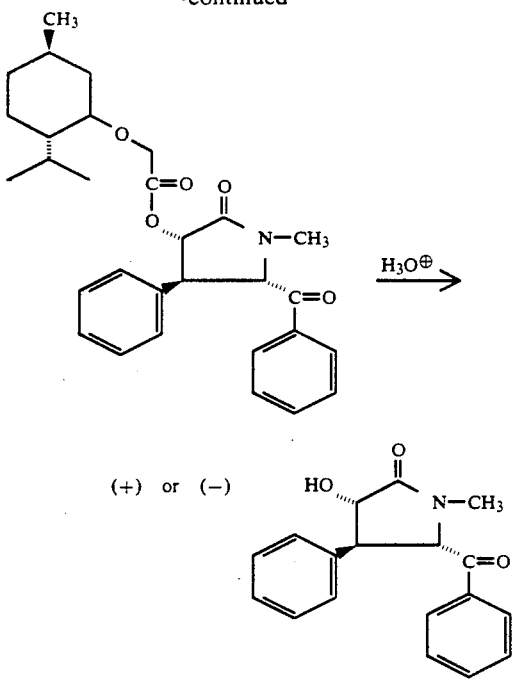

The compounds of the general formula (IVa) are known per se [compare DE-A1 3,431,257].

Suitable bases are organic amines such as triethylamine, picoline or N-methylpiperidine or pyridine. Pyridine is preferred.

The reaction is in general carried out in a temperature range from 0° C. to +60° C., preferably at room temperature.

The reaction is in general carried out at normal pressure. However, it is also possible to carry out the reaction at elevated or reduced pressure.

In order to remove the hydroxyl protective group, sulphonic acids having $C_1$-$C_4$-alkyl radicals or aryl radicals such as, for example, methanesulphonic acid, ethanesulphonic acid, benzenesulphonic acid or toluenesulphonic acid are in general used. Toluenesulphonic acid is preferred.

The reaction is carried out in a temperature range from +50° C. to +150° C., preferably at +80° C. to +130° C. and at normal pressure.

The compound of the formula (V) is known [compare Beilstein 9, 498].

2,6-Lutidine of the formula (VII) is also known [compare Beilstein 20, 244].

The compounds of the general formula (IVa) are known or can be prepared by known methods [compare DE-A1 3,537,075].

Diethyl azodicarboxylate is known [compare Experimentia, 25, 680 (1969); Tetrahedron 26, 5731 (1970)].

(−)-Menthoxyacetyl chloride of the formula (IX) is known and can be prepared from (−)-menthoxyacetic acid under the action of chlorinating agents such as, for example, thionyl chloride [compare Beilstein, 6 (1), 25].

The compounds of the general formula (Ib) have a pronounced cerebral hypoxia-protective and anti-amnesic action. They can therefore be employed as cerebral therapeutics and nootropics. In addition, the compounds of the general formula (Ib) according to the invention cause a reduction of increased glutamine pyruvate transaminase in the serum, in the case of cell damage. They can therefore be employed as medicaments for cardiac infarct, acute hepatitis, chronic hepatitis, pancreatitis or for muscle disorders.

The present invention includes pharmaceutical preparations which contain one or more active compounds according to the invention or which consist of one or more active compounds according to the invention in addition to non-toxic, inert, pharmaceutically suitable excipients and processes for the production of these preparations.

Non-toxic, inert, pharmaceutically suitable excipients are taken to mean solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders and sprays.

Tablets, coated tablets, capsules, pills and granules may contain the customary excipients, such as (a) fillers and extenders, for example starch, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calcium carbonate and sodium bicarbonate, (e) solution retardants, for example paraffin and (f) absorption accelerators, for example quaternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i) in addition to the active compound(s).

The tablets, coated tablets, capsules, pills and granules may be provided with the customary optical opacifying agent-containing coatings and shells and may also be composed such that they release the active compound(s), if appropriate with a delay, only or preferably in a certain part of the intestinal tract, in which case, for example, polymeric substances and waxes can be used as embedding materials.

If appropriate the active compound(s) may also be present in microencapsulated form with one or more of the abovementioned excipients.

Suppositories may contain the customary water-soluble or water-insoluble excipients, for example polyethylene glycols, fats, for example cocoa fat and higher esters (for example $C_{14}$-alcohol with $C_{16}$-fatty acid) or mixtures of these substances in addition to the active compound(s).

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound(s).

Powders and sprays may contain the customary excipients, for example lactose, talc, silica, aluminum hydroxide, calcium silicate and polyamide powder or mixtures of these substances in addition to the active compound(s). Sprays may additionally contain the customary propellants, for example chlorofluorohydrocarbons.

Solutions and emulsions may contain the customary excipients, such as solvents, solubilizers and emulsifiers, for example water, ethyl alcohol, isopropyl alcohol, ethyl carbonate, ethyl acetate, benzyl alcohol, dimethylformamide, oils, in particular cottonseed oil, groundnut oil, maize germ oil, olive oil, castor oil and sesame oil, glycerol, glycerolformal, tetrahydrofurfuryl alcohol, polyethylene glycols and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances in addition to the active compound(s).

The said formulation forms may also contain colorants, preservatives and also odor-improving and flavor-improving additives, for example peppermint oil and eucalyptus oil and sweeteners, for example saccharin.

The therapeutically active compounds should preferably be present in the abovementioned pharmaceutical preparations in a concentration of about 0.1 to 99.5, preferably 0.5 to 95% by weight, of the total mixture.

The abovementioned pharmaceutical preparations may also contain further pharmaceutical active compounds in addition to the active compounds according to the invention.

The production of the abovementioned pharmaceutical preparations takes place in a customary manner by known methods, for example by mixing the active compound(s) with the excipient(s).

In general, it has proved advantageous on intravenous administration to administer amounts of about 0.001 to 1 mg/kg, preferably about 0.01 to 0.5 mg/kg of body weight to obtain effective results, and on oral administration the dosage is about 0.01 to about 20, preferably 0.1 to 10 mg/kg of body weight.

In spite of this, it may be necessary to deviate from the amounts mentioned, depending on the body weight or the type of administration route, on individual behaviour towards the medicament, the manner of its formulation and the point in time or interval at which administration takes place. Thus, in some cases it may be sufficient to manage with less than the minimum amount previously mentioned, while in other cases the upper limit mentioned must be exceeded. In the case of the administration of relatively large amounts, it may be advisable to divide these into several individual doses over the course of the day.

STARTING COMPOUND

EXAMPLE I (−)-Menthoxyacetyl chloride

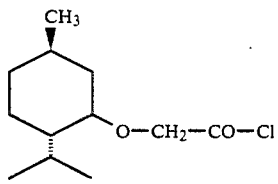

0.771 g (3.6 mmol) of (−)-menthoxyacetic acid is stirred under reflux with 2.1 g of thionyl chloride for 4 to 5 h. The thionyl chloride is first removed from the solution by distillation under reduced pressure. 3 ml of dry benzene are then added in order to remove residual thionyl chloride by means of vacuum distillation. 0.9 g of the title compound is obtained.

PREPARATION EXAMPLES

EXAMPLE 1

N-Methyl-N-phenacyl-3-phenylglycidamide

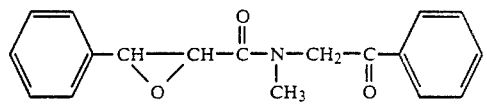

a) 2.4 g (0.0086 mol) of N-methyl-N-phenacyl cinnamamide and 8.6 g (0.04 mol) of m-chloroperbenzoic acid are dissolved in 170 ml of chloroform and allowed to stand at room temperature for 2 days. The precipitate is filtered off and the filtrate is washed successively with sodium sulphite solution (10%), sodium carbonate solution (10%) and water and dried over anhydrous sodium sulphate. The solvent is removed, the residue is dissolved in 6 ml of benzene/dry ether (1:1) and the solution is cooled in a refrigerator. After separating off unreacted starting material, the precipitate is filtered off. The oily residue is purified by chromatography.

Yield: 1.25 g (49.2% of theory).

Yield: 1.25 g (49.2% of theory).

$^1$H-NMR (90 MHz, CDCl$_3$): δ=3.09 (s)+3.21 (s, 3H, NCH$_3$); 3.49 (d)+3.88 (d, J=2.7 Hz, 1H); 4.04 (d)+4.15 (d, J=2.7 Hz, 1H); 4.82, 5.04 (AB, J=18 Hz)+4.96 (s, 2H); 7.30−7.8 (m, 8H); 8.01 (dd, J=1.8 Hz, 8 Hz)+8.06 (dd, J=2.7 Hz, 8 Hz, 2H).

b) 36 g of activated manganese dioxide are added with vigorous stirring to a solution of 5.94 g (0.02 mol) of N-methyl-N-(β-hydroxy-β-phenyl)ethyl-3-phenylglycidamide. The mixture is stirred for 1.5 h until starting material is no longer detectable in the thin-layer chromatographic checking. The manganese dioxide is filtered off and washed with methylene chloride. The combined filtrates are washed first with 20 ml of a 15% sodium hydrogen sulphite solution and 20 ml of a saturated sodium chloride solution and dried over anhydrous sodium sulphate. A viscous transparent residue is obtained, which solidifies on allowing to stand. White needles are obtained by recrystallization.

Yield: 4.42 g (75% of theory).

m.p. °C.: 76.5°–79° C.

After a second recrystallization, a melting point of 78.5°–80° C. is determined.

$^1$H-NMR (CDCl$_3$): δ=3.12 (s)+3.26 (s); (3H, NCH$_3$); 3.52 (d)+3.85 (d, 1H, J=2 Hz); 4.07 (d), 4.19 (d, 1H, J=2 Hz); 4.88 (d); 5.10 (d); (2H, J=18 Hz, PhCOCH$_2$); 7.30-8.16 (m, 10H).

EXAMPLE 2

(±) 3(S*), 4(R*),
5(S*)-1-Methyl-3-hydroxy-4-phenyl-5-benzoyl-pyrrolidin-2-one

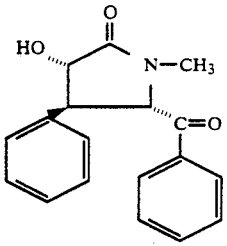

490 mg (1.66 mmol) of the compound Preparation Example 1 in 10 ml of tetrahydrofuran are added dropwise at −72° C. with stirring and cooling to a solution of 4 mmol of lithium diisopropylamide in 5 ml of tetrahydrofuran. The mixture is cooled and stirred over the course of 4 h, until starting material is no longer detectable. 100 ml of water are then added slowly. Tetrahydrofuran is removed in vacuo. 680 mg of a brown semisolid crude product are obtained, which is purified by chromatography (Chromatotron). Empirical formula: $C_{18}H_{17}NO_3$.

Elemental analysis: calc.: C 73.22, H 5.76, N 4.75. found: C 73.27, H 5.67, N 4.70.

$^1$H-NMR (CDCl$_3$): δ=2.92 (s, 3H, NCH$_3$); 3.92 (t, J=8.5 Hz, 1H, C$_4$H); 3.40 (br, s, 1H, exchangeable using D$_2$O); 4.93 (d, J=8.5 Hz, 1H, C$_3$-H); 5.50 (d, J=8.5 Hz, 1H, C$_5$-H); 7.04–7.84 (m, 10H, ArH).

EXAMPLE 3a AND b

1-Methyl-4-phenyl-5-benzoyl-pyrrolidin-2-one-3-yl (+)3(S*), 4(R*), 5(S*)-3-menthoxyacetate (Example 3a)

1-Methyl-4-phenyl-5-benzoyl-pyrrolidin-2-one-3-yl (−)3(S*), 4(R*), 5(S*)-3-menthoxyacetate (Example 3b)

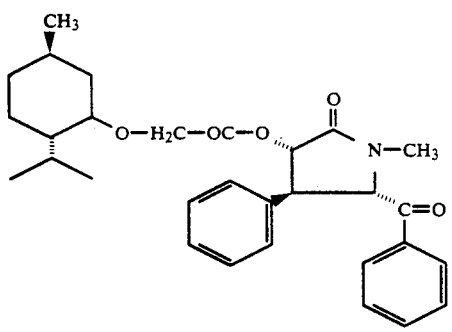

0.9 g of the compound from Starting compound Example 1 is dissolved in 10 ml of methylene chloride and 0.88 g (3 mmol) of racemate of the compound from Example 2 is then added. After dissolving, the reaction mixture is cooled in an ice bath and 0.5 ml of pyridine is added. The reaction solution is stirred at room temperature for 4 h. Thin-layer chromatographic examinations (SiO$_2$ plate) show two spots with R$_f$ values of 0.37 and 0.42 using the eluent system ether/hexane (2:1). The reaction solution is diluted with 10 ml of methylene chloride and successively neutralized by washing with 20 ml of 2N hydrochloric acid, saturated sodium carbonate solution and saturated sodium chloride solution. After drying over sodium sulphate, the solvent is removed and 1.69 g of a viscous solid are obtained, which is taken up in 200 ml of hexane and is converted into a fine powder by means of ultrasound. 0.747 g of a solid are obtained. After recrystallizing from methanol, 0.48 g (33% of theory) of the one diastereomer (3a) having a melting point of 171°–172.5° C. and R$_f$=0.4 is obtained.

$[α]_D^{15}$=52.6 (c=0.95 chloroform).

$^1$H-NMR (CDCl$_3$, 90 MHz): δ=0.64–2.40 (m, 18H, menthol H); 2.98 (s, 3H, N—CH$_3$); 3.1 (m, 1H); 3.32 (t, 1H, J=4.7 Hz, C$_4$—H); 4.09 (s, 2H, —O—CH$_2$—C=O); 5.04 (d, 1H, J=4.7 Hz, C$_5$—H); 5.40 (d, 1H, J=4.7 Hz, C$_3$—H); 7.10–7.70 (m, 10H, ArH).

The hexane solution is concentrated to give 0.81 g of an oily residue. This is chromatographed on a column loaded with 60 g of SiO$_2$. 0.6 g (41% of theory) of the other diastereomer (3b) of R$_f$=0.37 is obtained. After recrystallization from hexane, the solid has a melting point of 105°–106.5° C.

$[α]_D^{18}$=−32.9 (c=1.1 chloroform).

$^1$H-NMR (CDCl$_3$, 90 MHz): δ=0.64–2.40 (m, 18H, menthol H); 2.98 (s, 3H, NCH$_3$); 3.0–3.2 (m, 1H); 3.34 (t, 1H, J=5.0 Hz, C$_4$—H); 4.11 (s, 2H, —OCH$_2$—C=O); 5.06 (d, 1H, J=5·Hz, C$_5$—H); 5.46 (d, 1H, J=5 Hz, C$_3$—H); 7.00–7.70 (m, 10H, ArH).

EXAMPLES 4a AND b (+)-1-Methyl-3-hydroxy-4-phenyl-5-benzoyl-pyrrolidin-2-one (Example 4a)

(−)-1-Methyl-3-hydroxy-4-phenyl-5-benzoyl-pyrrolidin-2-one (Example 4b)

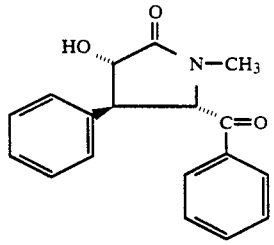

a) 404 mg (0.82 mmol) of one diastereomer from Example 3a are heated under reflux with 190 mg of p-toluenesulphonic acid in 40 ml of methanol and 10 ml of water for 7 h. The solvent is then removed. The residue which remains is dissolved in 30 ml of methylene chloride. The solvent is washed with saturated sodium bicarbonate solution and sodium chloride solution and dried over anhydrous sodium sulphate. After removing the solvent, a solid is obtained which crystallizes from the system ethyl acetate/hexane (5:2).

Yield: 210 mg (86% of theory), white needles.
m.p. °C.: 166°–169° C.
$[α]_D^{15}$=14.55 (c=0.54 in chloroform).
$^1$H-NMR (CDCl$_3$, 90 MHz): δ=2.40 (br, 1H, OH); 2.93 (s, 3H, NCH$_3$); 3.27 (t, 1H, J=7.0 Hz, C$_4$—H); 4.46 (d, 1H, J=7.0 Hz, C$_3$—H); 5.05 (d, 1H; J=7.0 Hz, C$_5$—H); 7.10–7.70 (m, 10H, ArH).

b) 442 mg of the other diastereomer from Example 3b are hydrolyzed in analogy to the procedure given under a). 217 mg of a white solid are obtained which crystallizes from the system ethyl acetate/cyclohexane.

Yield: 217 mg (82% of theory).
m.p. °C.: 170°–172° C.

[α]$_D^{15}$ = +15.3 (c=0.47 in chloroform).

$^1$H-NMR (CDCl$_3$, 90 MHz): δ=2.74 (br, 1H, OH); 2.92 (s, 3H, NCH$_3$); 3.27 (t, 1H, J=7.0 Hz, C$_4$—H); 4.46 (d, 1H, J=7.0 Hz, C$_3$—H); 5.05 (d, 1H, J=7.0 Hz, C$_5$—H); 7.10-7.70 (m, 10H, ArH).

EXAMPLES 5a, b AND c (±) 3(S*), 4(R*), 5(S*)-1-Methyl-3-tetrahydropyranyloxy-4-phenyl-5-benzoyl-pyrrolidin-2-one (Example 5a)

(+) 3(S*), 4(R*), 5(S*)-1-Methyl-3-tetrahydropyranyloxy-4-phenyl-5-benzoyl-pyrrolidin-2-one (Example 5b)

(−) 3(S*), 4(R*), 5(S*)-1-Methyl-3-tetrahydropyranyloxy-4-phenyl-5-benzoyl-pyrrolidin-2-one (Example 5c)

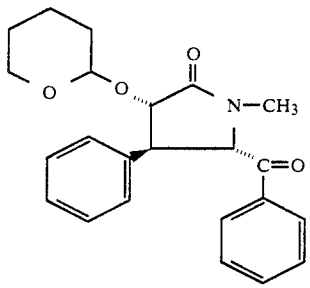

0.89 g (3 mmol) of the compound from Example 2, 4a or 4b is dissolved in 5 ml of methylene chloride, and 760 mg of 2,3-dihydropyran and 75 mg of pyridinium p-toluenesulphonate are then added. The reaction solution is stirred overnight at room temperature, and it is then checked by thin-layer chromatography whether the starting compound has completely reacted. 20 ml of methylene chloride are added and the solution is washed with sodium sulphate solution. The solution is dried over anhydrous magnesium sulphate. After concentrating the organic phase, a white solid is obtained. This is chromatographed on a silica gel column and the solid is recrystallized from methylene chloride/ether. 1.05 g (92% of theory) of the title compound are obtained.

m.p. °C.: 173°-175° C.

$^1$H-NMR (CDCl$_3$, 90 MHz): δ=1.2-2.0 (m, 6H); 2.93 (s, 3H, NCH$_3$); 3.10-3.48 (m, 3H, C$_4$—H); 4.46+4.64 (d+d, 1H, J=6.3 Hz, C$_3$—H); 4.97+4.95 (d+d, 1H, J=5.5 Hz, C$_5$—H); 5.17+4.10 (m+m, 1H); 7.10-7.70 (m, 10H, ArH).

The abovementioned procedure makes possible the preparation of the title compounds from the optically active 3(S*),4(R*),5(S*)-1-methyl-3-hydroxy-5-benzoyl-4-phenylpyrrolidin-2-one.

a) 0.51 g (90% of theory) of the corresponding ether having a melting point of 181°-187° C. are obtained from 0.443 g of the (−)-isomer (5c).

[α]$_D^{15}$ = +13.5 (c=0.42 in chloroform).

Epimer ratio: 2:1.

b) The (+)-isomer (5b) is obtained in an amount of 426 mg (91% of theory).

m.p. °C.: 194°-200° C.

[α]$_D^{15}$ = 11.9 (c=0.024 in chloroform).

Epimer ratio 1:1.

EXAMPLES 6a, b AND c (±) 3(S*), 4(R*), 5(S*)-1-Methyl-3-tetrahydropyranolyloxy-4-p-chlorophenyl-5-benzoyl-pyrrolidin-2-one (6a)

(+) 3(S*), 4(R*), 5(S*)-1-Methyl-3-tetrahydropyranolyloxy-4-p-chlorophenyl-5-benzoyl-pyrrolidin-2-one (6b)

(−) 3(S*), 4(R*), 5(S*)-1-Methyl-3-tetrahydropyranolyloxy-4-p-chlorophenyl-5-benzoyl-pyrrolidin-2-one (6c)

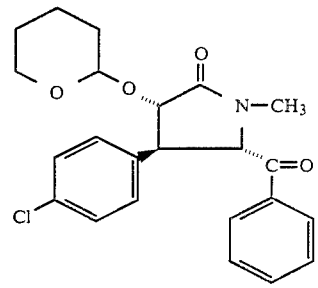

125 mg (0.5 mmol) of pyridinium p-toluenesulphonate and 15 ml (17 mmol) of 2,3-dihydropyran are added to a solution of 1.65 g (5.0 mmol) of (±)3(S*),4(R*),5(S*)-1-Methyl-3-hydroxy-4-p-chlorophenyl-5-benzoylpyrrolidin-2-one in 50 ml of dry methylene chloride. The reaction solution is stirred at room temperature for 7 h and worked up in analogy to the procedure of Example 5. 1.9 g of white crystals of melting point 123°-125° C. of R$_F$ value 0.71 in the eluent system ethyl acetate/hexane (2:1) are first obtained. These are recrystallized from tetrahydrofuran and isopropyl ether.

m.p. °C.: 129°-132° C.

EXAMPLES 7a, b AND c (±) 3(S*), 4(R*), 5(S*)-1-Methyl-3-tetrahydropyranolyloxy-4-p-fluorophenyl-5-benzoyl-pyrrolidin-2-one (7a)

(+) 3(S*), 4(R*), 5(S*)-1-Methyl-3-tetrahydropyranolyloxy-4-p-fluorophenyl-5-benzoyl-pyrrolidin-2-one (7b)

(−) 3(S*), 4(R*), 5(S*)-1-Methyl-3-tetrahydropyranolyloxy-4-p-fluorophenyl-5-benzoyl-pyrrolidin-2-one (7c)

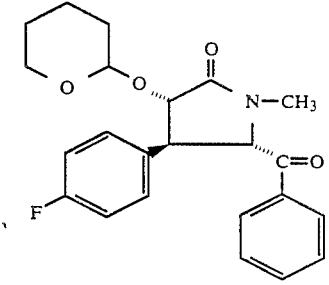

The title compound is prepared in analogy to the procedure of Example 6.

Yield: 1.84 g (93% of theory).

m.p. °C.: 159°-165° C.

Epimer ratio: 2:1.

EXAMPLES 8a, b AND c

3(S*), 4(R*), 5(S*)-1-Methyl-3-hydroxy-5-tosyloxybenzyl-pyrrolidin-2-one

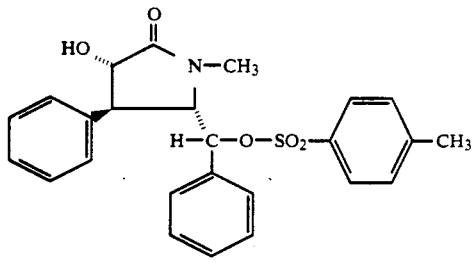

A solution of 0.190 g (0.5 mmol) of the compound from Example 7 in 5 ml of tetrahydrofuran is cooled to −10° C. and 1.5 ml of a 1M tetrahydrofuran solution of lithium tri-sec-butyl-borohydride (1.5 mmol) are added under a nitrogen atmosphere. The mixture is stirred at −10° C. for 1 h, then 190 mg (1.0 mmol) of p-chloro-toluenesulphonic acid in 2 ml of tetrahydrofuran are added and the mixture is allowed to stand overnight. The reaction solution is extracted three times using 10 ml of methylene chloride each time. The methylene chloride solution is neutralized by washing with 2N sodium hydroxide and sodium chloride solution. After drying over anhydrous sodium sulphate, the residue is filtered off and the solution is concentrated to dryness.

The residue is taken up in anhydrous ethanol and heated to 60° C.; 20 g of p-toluenesulphonic acid are then added in the course of 10 min and the mixture is cooled to −15° C. White needles of melting point 171°–172° C. are obtained.

$^1$H-NMR (CDCl$_3$, 90 MHz): δ=2.20 (1H, OH); 2.36 (s, 3H, Ar—CH$_3$); 2.84 (s, 3H, NCH$_3$); 3.15 (t, 1H, J=5.5 Hz, C$_4$—H); 3.90 (dd, 1H, J=4.0 Hz, 5.5 Hz, C$_5$—H); 4.14 (d, J=5.5 Hz, 1H, C$_3$—H); 5.69 (d, 1H, J=4 Hz, C$_7$—H); 6.80–6.95 (m, 2H, ArH); 7.0–7.25 (m, 10H, ArH); 7.56 (d, 2H, J=7.5 Hz, ArH).

Optically active 3(S*),4(R*),5(S*)-1-methyl-3-tetrahydropyranyloxy-4-phenyl-5-benzoyl-pyrrolidin-2-one are employed in the abovementioned procedure.

Starting from 379 mg (1.0 mmol) of the (−)-enantiomer (7c), 381 mg (84.3% of theory) of white crystalline optically active (+)3(S*),4(R*),5(S*),7(R*)-1-methyl-3-hydroxy-4-phenyl-5-(α-tosyloxy-benzyl)-pyrrolidin-2-one (8b) are obtained.

m.p. °C.: 157.5°–158.5° C.

[α]$_D^{15}$ = +52.3 (c=0.44 in chloroform).

The proton spectrum and the mass determination give identical results to the racemate.

Starting from 379 mg (1.0 mmol) of the (+)-enantiomer (7b), 377 mg of the corresponding tosylate are obtained.

m.p. °C.: 157.5°–158° C.

[α]$_D^{17}$ = −51.2 (c=0.32 in chloroform).

The spectra ($^1$H-NMR and IR) are identical with those of the abovementioned (−)-enantiomer (7c).

EXAMPLE 9

(+)-1-Methyl-3-hydroxy-4-p-chloro-phenyl-α-(p-tosyloxy-benzyl)-pyrrolidin-2-one

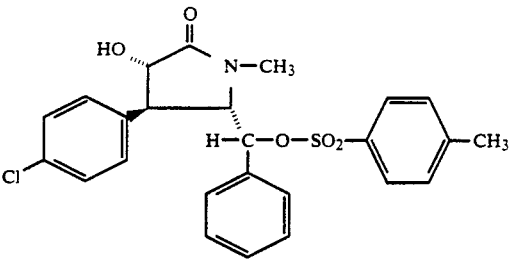

A solution of 1.24 g of (+)-1-methyl-3-tetrahydropyranyloxy-4-p-chlorophenyl-5-benzoyl-pyrrolidin-2-one (6b) in 20 ml of anhydrous tetrahydrofuran is slowly added dropwise at −25° C. to −30° C. with stirring to a precooled 1.0M lithium tri-sec-butylborohydride solution in tetrahydrofuran. The mixture is then stirred for a further 2 h. 860 mg of tosyl chloride in 4 ml of tetrahydrofuran are then added at −25° C. to −30° C., and the mixture is stirred at this temperature for a half hour and at room temperature for 2 h. The reaction solution is allowed to stand overnight. The reaction solution is added to 35 ml of ice water and extracted 3 times using 25 ml of benzene each time. The collected organic phases are washed with dilute hydrochloric acid, dilute sodium hydroxide solution and sodium bicarbonate solution and dried over sodium sulphate. The residue is filtered off and the filtrate is concentrated almost to dryness. 15 ml of anhydrous ethanol and 50 mg of p-toluenesulphonic acid are added to the residue which remains. The reaction solution is heated to 60° C. for 25 min. After filtration, white needles are obtained which are washed with ether.

Yield: 1.3 g (89% of theory).

m.p. °C.: 179°–180° C.

$^1$H-NMR (CDCl$_3$, 90 MHz): δ=1.93 (1H, OH); 2.37 (s, 3H, Ar—CH$_3$); 2.84 (s, 3H, NCH$_3$); 3.18 (t, 1H, J=6 Hz, C$_4$—H); 3.83 (dd, 1H, J=4 Hz, C$_5$—H); 4.09 (d, 1H, J=6 Hz, C$_3$—H); 5.70 (d, 1H, J=4 Hz, C$_7$—H); 6.6–7.6 (m, 13H, ArH).

EXAMPLE 10

(±)-1-Methyl-3-hydroxy-4-p-fluorophenyl-5-α-(p-tosyloxy-benzyl)pyrrolidin-2-one

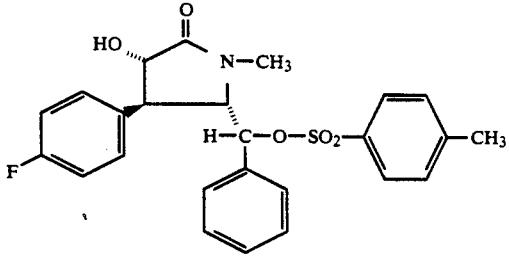

The title compound is obtained from 1.19 g of the compound from Example 6a in analogy to the procedure of Example 9.

Yield: 1.19 g (84.3% of theory).

m.p. °C.: 162°–164° C.

EXAMPLES 11a, b AND c (±) 11a; (+) 11b; (−) 11c Dehydrocycloclausenamide

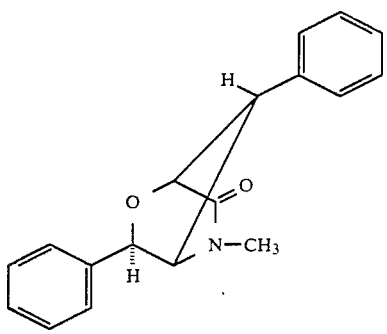

a) A solution of 1.35 g (3 mmol) of the compound from Example 8a, 8b or 8c in 100 ml of 2,6-lutidine is heated slightly with stirring under a nitrogen atmosphere over the course of 5 h. 170 ml of methylene chloride are then added. The reaction solution is washed successively with 30 ml of water and 3 times with 40 ml each of 6N hydrochloric acid, water, saturated sodium carbonate and saturated sodium chloride solution. After drying over anhydrous sodium sulphate and filtering, the solvent is removed and 0.914 g of a brown oily residue is obtained. This solidifies on allowing to stand and is crystallized from 4 ml of methanol.

The white precipitate has a melting point of 158°-159° C. After chromatography on a column loaded with 30 g of SiO$_2$, 450 mg of crystalline product of melting point 164°-166° C. are obtained. This melting point is identical to that of (−)-dehydrocycloclausenamide. A further 100 mg of the title compound can be obtained from the filtrate from the chromatography.

Total yield: 550 mg (66% of theory).
Empirical formula: $C_{18}H_{17}NO_2$.
Elemental analysis: calc.: C 77.39, H 6.14, N 5.02. found: C 77.30, H 5.84, N 4.92.

$^1$H-NMR (CDCl$_3$, 300 MHz): δ=2.96 (s, 3H, NCH$_3$); 3.615 (s, br, 1H, C$_4$—H); 4.101 (1H, C$_5$—H); 4.835 (dd, 1H, J=1.2 Hz, 2.7 Hz, C$_3$—H); 5.014 (s, 1H, C$_7$—H); 7.0-7.5 (m, 10H, ArH).

b) A solution of 0.174 g (1 mmol) of diethyl azodicarboxylate in 3 ml of tetrahydrofuran is added dropwise at room temperature to a solution of neoclausenamide (0.297 g, 1 mmol) and 0.262 g (1 mmol) of triphenylphosphane in 6 ml of tetrahydrofuran in the course of 2 h. The mixture is stirred for 24 h and the white precipitate is then filtered off. The filtrate is concentrated in vacuo and the residue which remains is purified by preparative thin-layer chromatography in the eluent system chloroform/methanol (9:1). 87 mg (31% of theory) of the title compound are obtained. The R$_f$ values and the IR, $^1$H-NMR and mass spectroscopy data are identical to those of the naturally obtained product. The specific rotation of +0.00 of the synthetically prepared compound shows this to be the racemate.

$^1$H-NMR (CDCl$_3$, 90 MHz): δ=2.95 (s, 3H, NCH$_3$); 3.60 (s, 1H, C$_4$—H); 4.09 (s, 1H, C$_5$—H); 4.81 (s, 1H, C$_3$—H); 5.00 (s, 1H, C$_7$—H); 7.1-7.5 (m, 10H, ArH).

Optically Active Isomers

Starting from 640 mg of the compound from Example 8b, 255 mg (64.4% of theory) of Example 11b are obtained by recrystallization from methanol and chromatography of the mother liquor.

m.p. °C.=199°-199.5° C.

$[α]_D^{15}$=−88.3 (c=0.14 in methanol).

For comparison, the naturally obtained product has the melting point: 164°-166° C.

$[α]_D^{15}$=−40.0 (c=0.23 in methanol).

$^1$H-NMR (CDCl$_3$, 90 MHz): δ=2.94 (s, 1H, NCH$_3$); 3.58 (s, 1H, C$_4$—H); 4.05 (s, 1H, C$_5$—H); 4.77 (m, 1H, C$_3$—H); 4.97 (s, 1H, C$_7$—H); 6.98-7.48 (m, 10H, ArH).

Starting from 225 mg of the compound from Example 8c, 77 mg (55% of theory) of the (−)-enantiomer 11c are obtained by recrystallization.

m.p. °C.: 204°-204.5° C.

$[α]_D^{15}$=+86.2 (c=0.13 in methanol).

$^1$H-NMR (CDCl$_3$, 90 MHz): δ=2.93 (s, 3H, NCH$_3$); 3.56 (s, 1H, C$_4$—H); 4.04 (s, 1H, C$_5$—H); 4.86 (m, 1H, C$_3$—H); 4.96 (s, 1H, C$_7$—H); 6.97-7.44 (m, 10H, ArH).

EXAMPLE 12

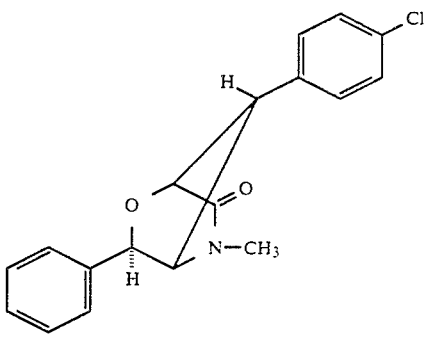

0.97 g (2.0 mmol) of 1-methyl-3-hydroxy-4-p-chlorophenyl-5-(α-tosyloxybenzyl)-pyrrolidin-2-one (8a) are dissolved in 75 ml of 2,6-lutidine. The mixture is stirred at 145° C. for 5 h. Lutidine is then removed by distillation and the residue which remains is taken up in 60 ml of chloroform and washed twice successively with 10 ml of 4N hydrochloric acid, 20 ml of water, saturated sodium carbonate and sodium chloride solution and dried over anhydrous sodium sulphate. After filtering off and removing the solvent, a brown oily residue is obtained which is eluted in the eluent system chloroform/acetone (100:3) on a column loaded with 40 g of SiO$_2$. 430 mg of a solid are obtained, whose thin-layer chromatographic examination shows two R$_f$ values 0.64 and 0.56. The solid is recrystallized using isopropanol and gives a crystalline product of 337 mg (53% of theory) having a melting point of 158°-160° C. and an R$_f$ value=0.56.

$^1$H-NMR (CDCl$_3$, 90 MHz): δ=2.94 (s, 3H, NCH$_3$); 3.53 (s, 1H, C$_4$—H); 4.03 (s, 1H, C$_5$—H); 4.76 (m, 1H, C$_3$—H); 4.98 (s, 1H, C$_7$—H); 6.94-7.46 (m, 9H, ArH).

EXAMPLE 13

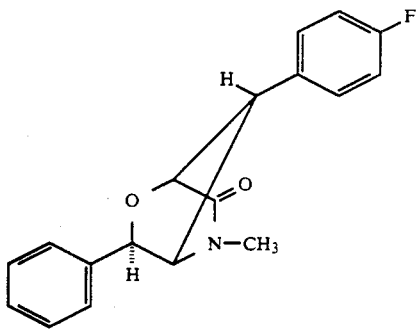

Starting from 944 mg (2.01 mmol) of the compound from Example 8a, the title compound is prepared in analogy to the procedure for Example 12.

Yield: 342 mg (57.7% of theory).

m.p. °C.: 163°-164° C.

$R_f$=0.51 (SiO$_2$ plate, chloroform/acetone 100:3).

$^1$H-NMR (CDCl$_3$, 90 MHz): δ=2.95 (s, 3H, NCH$_3$); 3.54 (s, 1H, C$_4$—H); 4.03 (s, 1H, C$_5$—H); 4.76 (s, 1H, C$_3$—H); 4.98 (s, 1H, C$_7$—H); 6.80-7.50 (m, 9H, ArH).

What is claimed is:

1. Process for the preparation of a compound of the formula

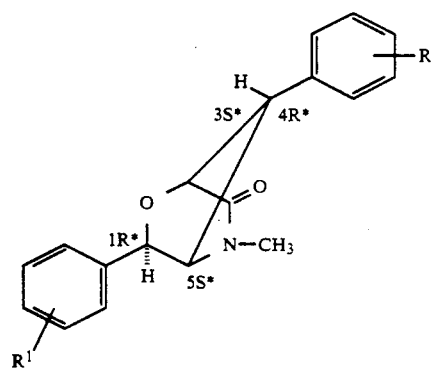

in which R and R$^1$ each independently represent hydrogen or halogen, as the racemate (±), as (+)- or as (−)-enantiomer, comprising

[A] etherifying a compound of the formula

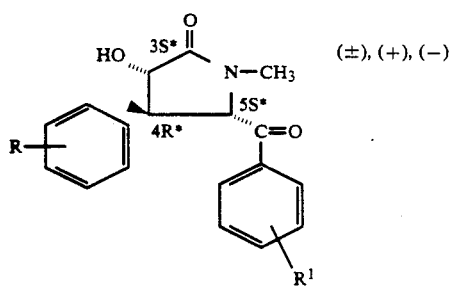

either as the racemate (±) or as the corresponding (+)-or (−)-enantiomer, with 2,3-dihydropyran to give a compound of the formula

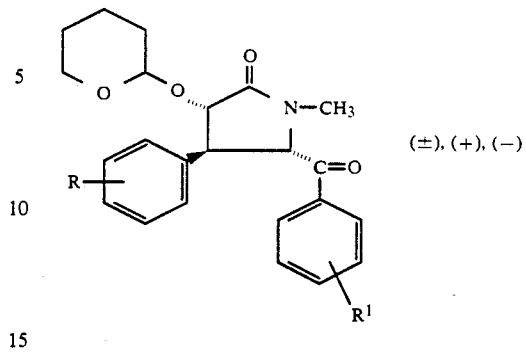

reducing the dihydropyranyl compound with a metal hydride or complex metal hydride to give a compound of the formula

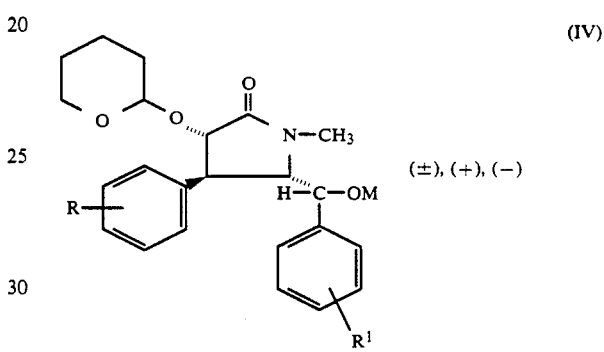

in which

M represents a metal, reacting the reduction product with p-methyltoluenesulphonyl chloride to give a compound of the formula

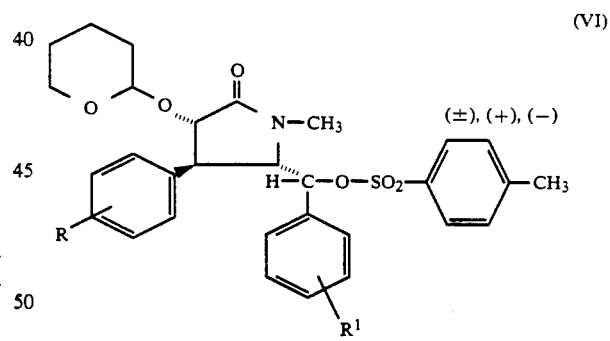

removing the tetrahydropyranyl protective group from the tosylate and reacting with 2,6-lutidine, or

[B] reacting a compound of the formula

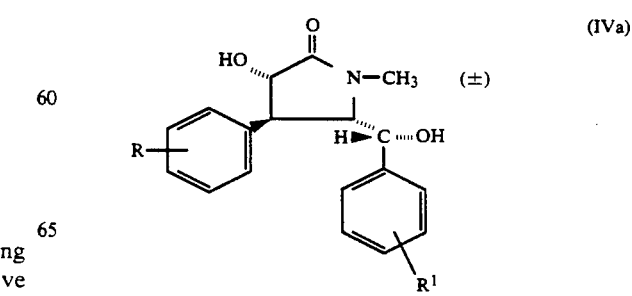

in the racemic form (±) with diethyl azodicarboxylate.

2. Process according to claim 1, wherein the etherification is carried out in a temperature range from −10° C. to +50° C.

3. Process according to claim 1, wherein the reduction is carried out using lithium borohydride, sodium borohydride, lithium aluminum hydride, zinc borohydride or aluminum triisopropoxide as the reducing agent.

4. Process according to claim 1, wherein a protonic acid is employed for the removal of the tetrahydropyranyl protective group.

5. Process according to claim 4, wherein the protonic acid is hydrochloric acid or sulphuric acid.

6. Process according to claim 1, wherein a trialkylphosphane is employed as an auxiliary for the reaction with azodicaroxylic acid ester.

7. A compound of the formula

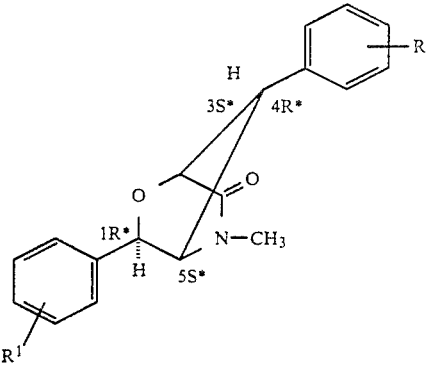

in which
R³ represents halogen and
R¹ represents hydrogen or halogen, as the racemate (±) and as (+)- or (−)-enantiomers.

8. A pharmaceutical composition useful as a cerebral therapeutic, nootropic or in the reduction of increased glutamine pyruvate transaminase in serum comprising a compound according to claim 7, and non-toxic, inert, pharmaceutically suitable excipients.

9. A method of treating cerebral hypoxia comprising administering to a patient in need of such treatment an effective amount of a compound according to claim 7.

10. A method of treating amnesia comprising administering to a patient in need of such treatment an effective amount of a compound according to claim 7.

11. A method of reducing increased glutamine pyruvate transaminase in serum comprising administering to a patient in need of such reduction an effective amount of a compound according to claim 7.

* * * * *

＿

UNITED STATES PATENT AND TRADEMARK OFFICE
CERTIFICATE OF CORRECTION

PATENT NO. : 5,093,350

DATED : March 3, 1992

INVENTOR(S) : Huang et al.

It is certified that error appears in the above-identified patent and that said Letters Patent is hereby corrected as shown below:

Col. 21, line 58   Delete " 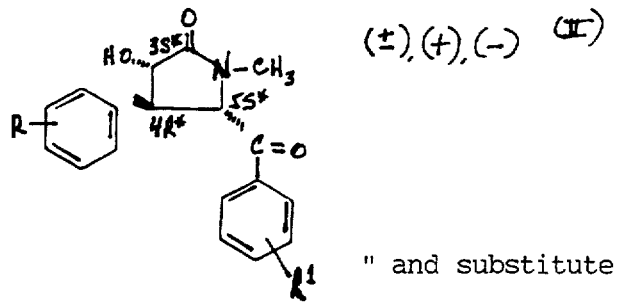 " and substitute

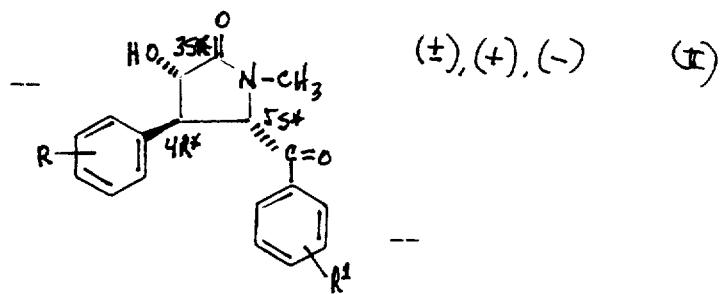

Col. 24, line 4   Delete " 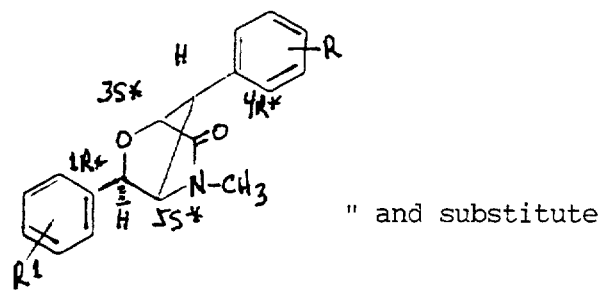 " and substitute

UNITED STATES PATENT AND TRADEMARK OFFICE
CERTIFICATE OF CORRECTION

PATENT NO. : 5,093,350

DATED : March 3, 1992

INVENTOR(S) : Huang et al.

It is certified that error appears in the above-identified patent and that said Letters Patent is hereby corrected as shown below:

Col. 24, line 4 Cont'd

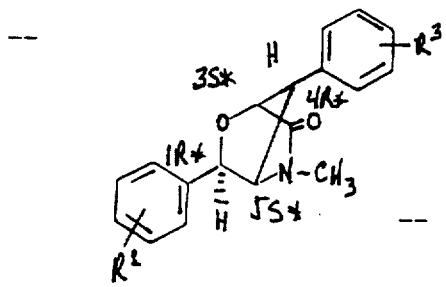

Signed and Sealed this

Fourteenth Day of December, 1993

Attest:

BRUCE LEHMAN

*Attesting Officer*   *Commissioner of Patents and Trademarks*